United States Patent
Santos

(10) Patent No.: US 9,248,552 B2
(45) Date of Patent: Feb. 2, 2016

(54) STRUCTURAL ARRANGEMENT FOR USE IN AN EXTRACTOR OF DISPOSABLE SYRINGE NEEDLES

(71) Applicant: Josemar Souza dos Santos, Porto Alegre (BR)

(72) Inventor: Josemar Souza dos Santos, Porto Alegre (BR)

(*) Notice: Subject to any disclaimer, the term of this patent is extended or adjusted under 35 U.S.C. 154(b) by 381 days.

(21) Appl. No.: 13/854,880

(22) Filed: Apr. 1, 2013

(65) Prior Publication Data

US 2013/0212851 A1    Aug. 22, 2013

Related U.S. Application Data

(63) Continuation of application No. PCT/BR2011/000170, filed on May 31, 2011.

(30) Foreign Application Priority Data

Oct. 15, 2010   (BR) .................................. 9001764 U

(51) Int. Cl.
  *B25B 7/02*      (2006.01)
  *A61M 5/32*      (2006.01)
  *A61M 5/158*     (2006.01)

(52) U.S. Cl.
  CPC ................ *B25B 7/02* (2013.01); *A61M 5/3205* (2013.01); *A61M 5/3278* (2013.01); *A61M 2005/1583* (2013.01); *Y10T 29/53909* (2015.01)

(58) Field of Classification Search
  CPC ............ A61M 5/3205; A61M 5/3202; A61M 5/3204; A61M 5/3278; A61M 2005/1583; A61M 2005/3208; A61M 2005/3215
  See application file for complete search history.

(56) References Cited

U.S. PATENT DOCUMENTS

| 4,275,628 | A | * | 6/1981 | Greenhouse | ........ A61M 5/3278 83/167 |
| 4,531,437 | A | * | 7/1985 | Szablak | .............. A61M 5/3278 241/100 |

(Continued)

FOREIGN PATENT DOCUMENTS

| BR | PI91031761 | 2/1993 |
| BR | PI9303667-1 A | 3/1994 |

(Continued)

OTHER PUBLICATIONS

PCT/BR2011/000170; WO 2012/048393 Pub Date: Apr. 19, 2012; includes International Search Report and International Application Status Report.

*Primary Examiner* — Monica Carter
*Assistant Examiner* — Seahee Yoon
(74) *Attorney, Agent, or Firm* — Peter Ganjian; Patent Law Agency, LLC

(57) ABSTRACT

A structural arrangement for use in an extractor of disposable syringe needles uses a needle extraction means with two interlocking parts (11 and 12) that move in a pincer-like manner, gripping the needle. A lateral lever (1) causes the inner pair of pincers of the device to move downwards, extracting the needle from the plastic tip. A capsule (6) for containing the needles removed from the plastic tips can be introduced into the lower portion of the body of the extractor. The top of the extractor is provided with a cover (2) that can be lifted for introducing the plastic tip into the device, with no contact of any kind between the operator and the needle. The upper portion of the extractor, when it is closed with the cover, has a funnel-shaped geometry (14), which prevents the user from accidentally pricking his or her hand when placing a syringe in the device in order to extract the needle.

1 Claim, 3 Drawing Sheets

(56) References Cited

U.S. PATENT DOCUMENTS

| | | | |
|---|---|---|---|
| 4,807,344 A * | 2/1989 | Kelson | A61M 5/3205 206/366 |
| 4,986,811 A * | 1/1991 | Thead et al. | 604/110 |
| 4,989,307 A * | 2/1991 | Sharpe et al. | 29/240 |
| 4,995,871 A | 2/1991 | Sasaki et al. | |
| 5,069,667 A | 12/1991 | Karmen | |
| 5,275,280 A | 1/1994 | Everhart | |
| 5,312,346 A * | 5/1994 | Han | 604/110 |
| 6,036,671 A * | 3/2000 | Frey | 604/110 |
| 6,545,242 B1 * | 4/2003 | Butler | A61M 5/3278 219/68 |
| 6,745,898 B2 * | 6/2004 | Lin | A61M 5/3278 206/366 |
| 6,792,662 B2 * | 9/2004 | Samuel | A61M 5/3205 206/366 |
| 6,909,251 B2 * | 6/2005 | Cooley | A61M 5/3205 318/139 |
| 7,389,873 B2 * | 6/2008 | Johnson aka Mindes | 206/366 |
| 9,011,385 B2 * | 4/2015 | Bianco et al. | 604/178 |
| 2005/0236289 A1 * | 10/2005 | Tanaka | A61M 5/3205 206/366 |
| 2005/0269226 A1 * | 12/2005 | Erickson et al. | 206/366 |
| 2005/0288636 A1 * | 12/2005 | Gerald Cooley et al. | 604/187 |

FOREIGN PATENT DOCUMENTS

| | | |
|---|---|---|
| BR | MU77004620 | 11/1998 |
| BR | MU76032205 | 10/1999 |
| BR | PI98042041 | 5/2000 |
| BR | MU85009822 | 12/2006 |
| BR | MU8702007-6 | 3/2009 |

* cited by examiner

STRUCTURAL ARRANGEMENT FOR USE IN AN EXTRACTOR OF DISPOSABLE SYRINGE NEEDLES

CROSS-REFERENCE TO RELATED APPLICATIONS

This Application is a CONTINUATION application claiming the benefit of priority of the co-pending International Patent Application No. PCT/BR2011/000170 with an international filing date of 31 May 2011 that designated the United States, which claims the benefit of priority of Federal Republic of Brazil Application No. MU9001764-1, filed 15 Oct. 2010, the entire disclosures of all Applications are expressly incorporated by reference in their entirety herein.

TECHNICAL FIELD OF THE MODEL

The description report that follows for the present application for a utility model regards to the development of a constructive arrangement applied to a remover of needles from disposable syringes which comprises the use of a means for removing said needle by interlocking two parts that move in a pincer-like manner and grip the needle. A lateral lever is released when the upper lid of the device is opened by pressing it with the thumb, said lever activated by the user's hand causing the inner pair of pincers to move pulling the needle inserted in the device and separating the metal portion (needle) from the plastic tip. One of the containers for exclusive containment of needles (metallic portion) removed from the plastic tips is disposed in the lower portion of the body of the needle remover, said containers having an anti-spill system that fits precisely into the mechanism which causes the device to lock when it is absent; a lid is disposed at the bottom to make the compact container (CC 75 needles) more resistant while in use and to close (seal) it after use. In an alternative embodiment, the device comprises a large container (LC 750 needles) and can be used under flat surfaces with no need for facilities and can store more than 750 needles, thus facilitating collective use. The needle remover has an opening at the center which allows viewing the containers as they fill up with no contact whatsoever between needles and the user. The upper portion of the needle remover closed by the lid is shaped in the form of a funnel after the aligner making it easier for the user to insert the needle and place the syringe in the device to activate it in a quick and safe manner.

STATE OF THE ART

The disposal of hospital waste is a problem that requires a complex solution because it involves delicate logistics ranging from the capture of contaminated material to their proper final disposal. Sharps such as needles and scalpels require delicate handling especially after use because, in case of an accident, contamination poses a real problem. Several devices for disposing of used needles are known in the art.

One such device known in the art is called NEX and recycles sharps waste such as needles and plastic. The syringe is placed in one part of the device which separates and stores the metallic portion (needle). The needle drops into the inner container. The plastic is stored in another part of the device.

After separation, NEX raises the temperature in both compartments by 1680°, thus sterilizing and melting the parts of the syringe. Any kind of organism is killed during the process. Molten steel and plastic are transformed into blocks that may be sold or recycled.

The prior art search relevant to the technical field of this utility model revealed patents that address this issue.

BR 7.603.220-5 by RIBEIRO (1996) describes a remover of disposable syringe needles, comprising a solid body formed from equal and symmetrical parts with lateral contour edges consisting of pegs and openings, configuring a tight dowel joint and sealed by thermal welding. The body has a rectangular-shaped anterosuperior opening through which an activating button is fitted. The button acts next to the area of the circular orifice on the frontal surface on which a guide member having a needle receiving orifice is disposed. The needle is inserted through both orifices to cause the button to go back upwards misaligning said orifices by an elastic means and removing the plastic and the needle from the syringe. The opening of the guide member usually remains closed as the button of the guide member goes back to its inoperative position.

BR 8.500.982-2 by SANTOS (2005) describes a compact needle remover comprising a cylindrical tank whose body narrows toward the opening for inserting the needle, having an area aligned toward the container that store removed needles after opening the compartment which is sealed and has a locking member at one extremity and a hinge at the other extremity, said container having harmonized wing geometry sealed to facilitate handling when transported or fastened to its movable support which has a lever for better operation and a hook for fastening. Moreover, the material used to reinforce the container can be the same as that of the needle to ensure complete recycling.

BR 8.702.007-6 by BEZERRA (2007) describes a needle remover which is fastened to the wall and connected to a sharps disposal box, comprising a hollow, conical cup and with different taper angles. There is a slot in the frontal part of the hollow cup into which a syringe with a needle is inserted. The upper opening is larger and is fitted into the sharps disposal box; the lengthener is in the back portion with a locking support.

BR 9.103.176-1 by CABRAL (1991) reveals a needle removal and disposal device comprising a container that allows the user to remove and dispose of needles with no contact with the used needle. The upper opening allows inserting the discarded material making impossible to have any contact with it and preventing the needles that have already been used to be reused.

AR 323.098 by SANTANGELO (1993) describes an remover of disposable syringe needles or the like, comprising a first device or removing device itself formed of a first body or a flat circular body disposed concentrically with relation to it; a second device or a temporary occlusion device formed of a cylinder portion whose external circumference is slightly smaller than the internal circumference of the cylindrical body, and a third device or a permanent occlusion device essentially formed of a flat circular body.

BR 9.804.204-1 by BIRKHAM et al. (1998) describes a container and a needle remover, and, more specifically, a container for infected sharps waste such as needles and scalpels, fitted with a system for disabling needles and a removing device. Said container is unpuncturable and can be taken to the incinerator for the destruction of the contaminated material.

U.S. Pat. No. 6,745,898 by LIN (2004) reveals a needle remover and a recovery device comprising a means for removing syringe needles and a box for storing them.

US 2002/0115987 by HILDWINE (2002) reveals a cannula needle remover and an extractor.

U.S. Pat. No. 5,947,950 by SHILLINGTON et al. (1998) reveals a needle removing device that uses movable gears.

Cited Documents: BR 7.603.220-5; AR 323.098; BR 7.700.462-0;

DISCUSSION

The removers revealed in the previous art perform a partial extraction of the needle and there is a need for a container that can be attached to the device or not.

The needle is always extracted by a means that grips the needle and deforms it with a plastic tip, shears or disposes of both (steel and plastic). Said means needs to be larger, requires necessary facilities, proper places and/or some kind of energy (electric) to function, thus increasing the period of time during which users are exposed to sharps before they are properly disposed of.

SHILLINGTON describes a needle remover that uses gear to remove the needle from the syringe tip. The removed needle drops into a disposable box. LIN uses a similar process in which the needle is removed and stored in a container. Other removing means and devices use similar systems.

The needle remover proposed herein uses a means for removing said needle by interlocking two parts that move in a pincer-like manner in order to grip the needle. After the hinged upper lid is opened, an internal lock is moved and the lever is released. After the lid is opened, the needle can be inserted inside the needle remover. The lever is moved by pressing it with the thumb. Said lever activated by the user's hand causes the inner pair of pincers of the device to move pulling the needle inserted in the device by the aligner, thus separating the metallic portion (needle) from the plastic tip. One of the containers for exclusive containment of needles (metallic portion) removed from the plastic tips is disposed in the lower portion of the body of the needle remover. The containers have an anti-spill system that fits precisely into the mechanism, locking the device when it is absent. A lid is disposed at the bottom to make the compact container more resistant (CC 75 needles) when in use and to close (seal) it after use. In an alternative embodiment, the device contains a large container (LC 750 needles) and can be used under flat surfaces with no need for facilities and can store more than 750 needles, thus facilitating collective use. The needle remover has an opening at the center which allows viewing the container as they fill up with no contact whatsoever between needles and the user. The upper portion of the needle remover closed by the lid is shaped in the form of a funnel after the aligner making it easier for the user to insert the needle and place the syringe in the device to activate it in a quick (5 seconds) and safe manner.

DESCRIPTION OF DRAWINGS

The characterization of the present document for the utility model patent now proposed is done by illustrative drawings of constructive arrangement applied to remover of needles from disposable syringes in such a way that the device can be entirely reproduced by using proper technique, allowing for the full characterization of the functionality of the pleaded object.

The descriptive part of the report is based on the drawings, which represent the best or preferred embodiment form of the object now idealized, through detailed and consecutive numbering, which makes clear the aspects that may be implied by the representation adopted, in order to clearly identify the protection now intended.

These drawings are merely illustrative and may present variations, provided that they do not depart from the initially pleaded.

Figure 1:
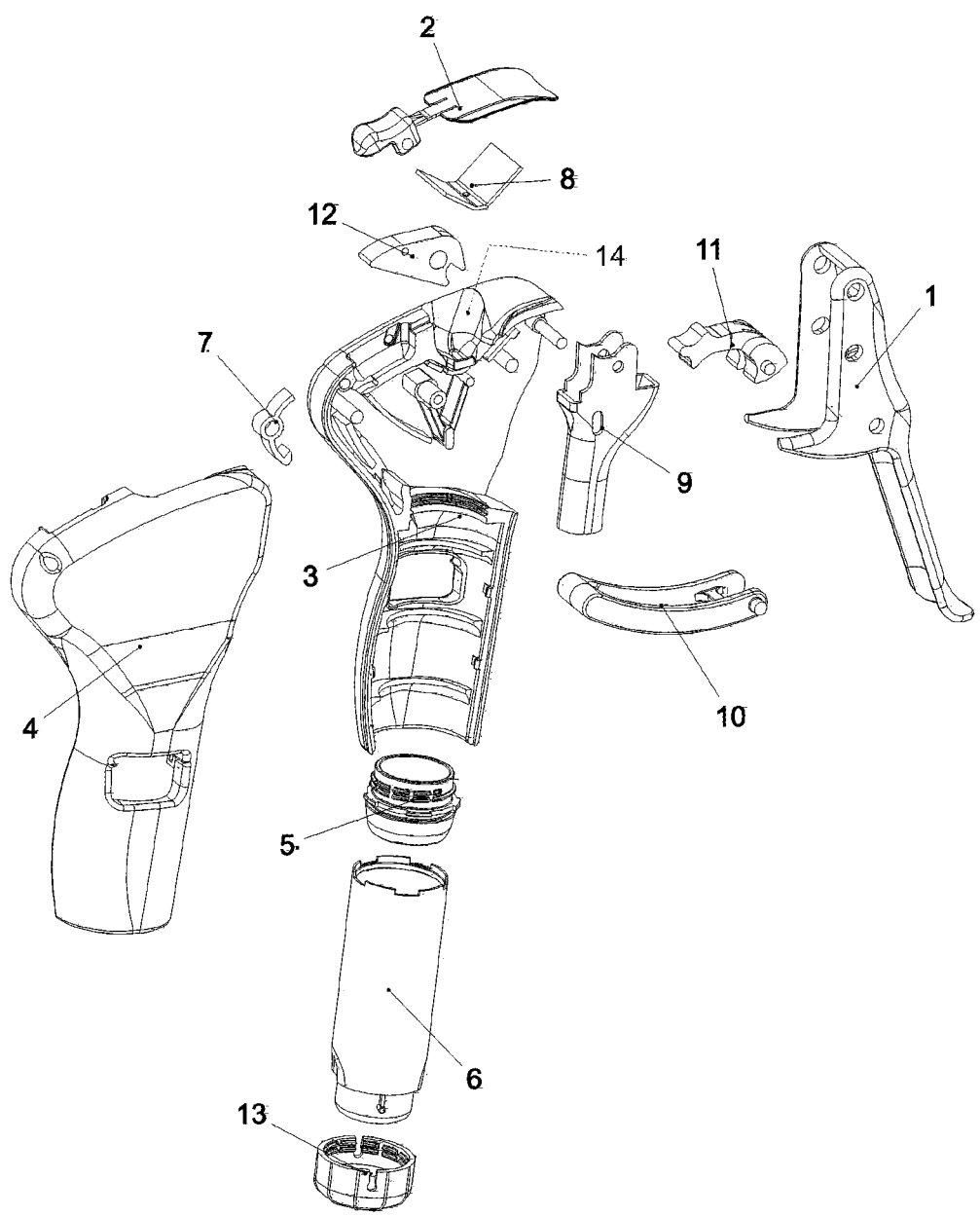
Figure 4:
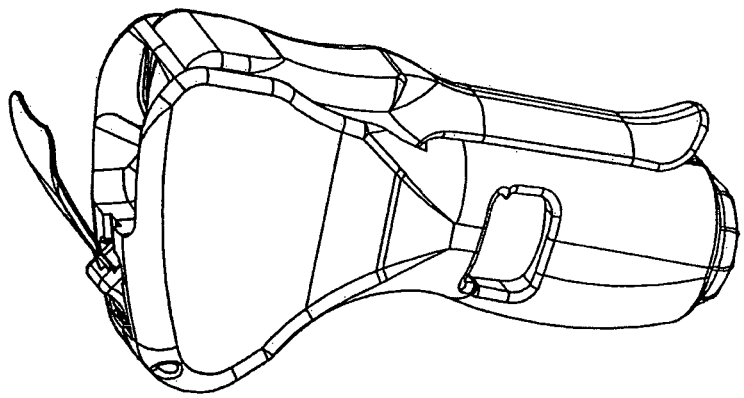
Figure 3:
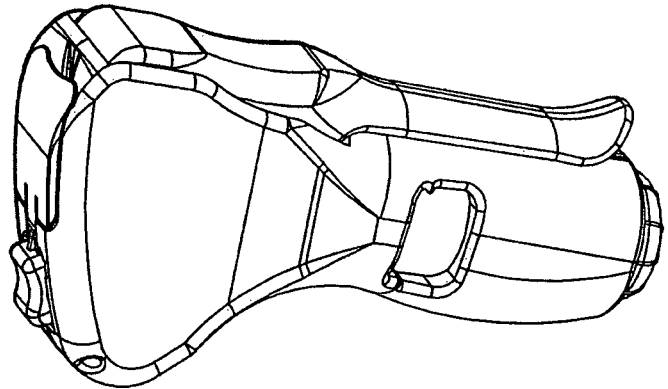
Figure 2:
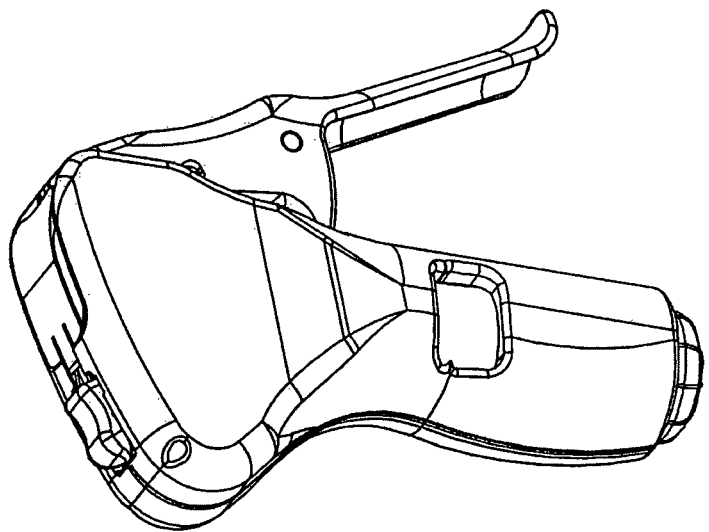

So, there is:

FIG. 1 is a perspective exploded view of the needle remover proposed herein in which the parts and their positions can be seen;

FIG. 2 is a perspective view of the needle remover with the lever in the lifted position;

FIG. 3 is another perspective view of the needle remover;

FIG. 4 is a perspective view of the needle remover with the upper lid in the opened position.

Figure 5:
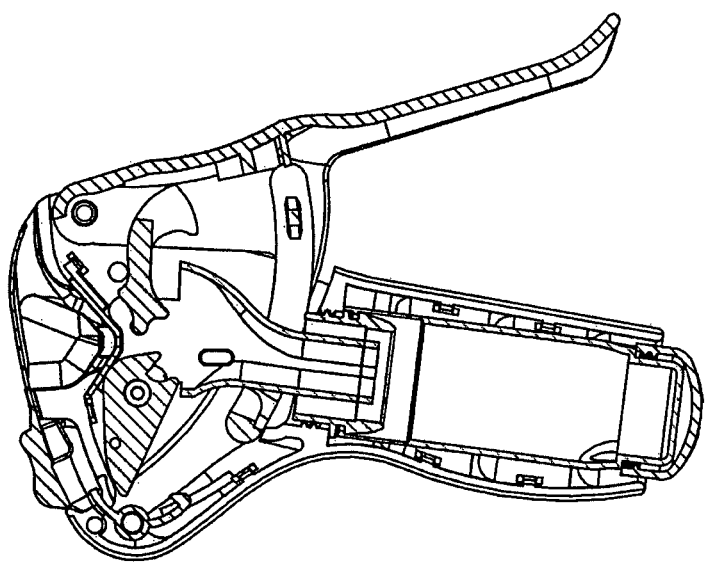

FIG. 5 is a longitudinal-section view showing the inner mechanism with the lever in the lifted position.

Figure 6:
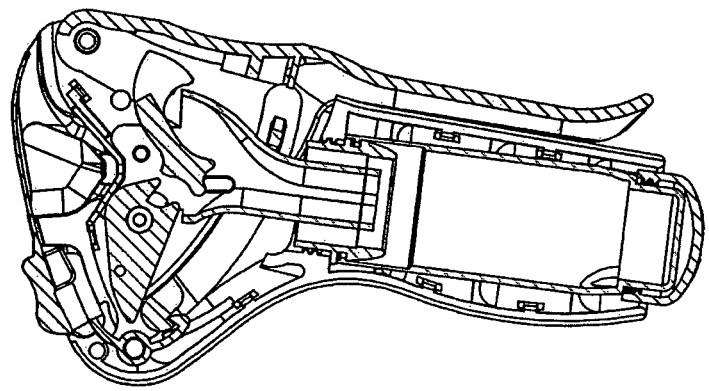

FIG. 6 is a longitudinal-section view; and

Figure 7:
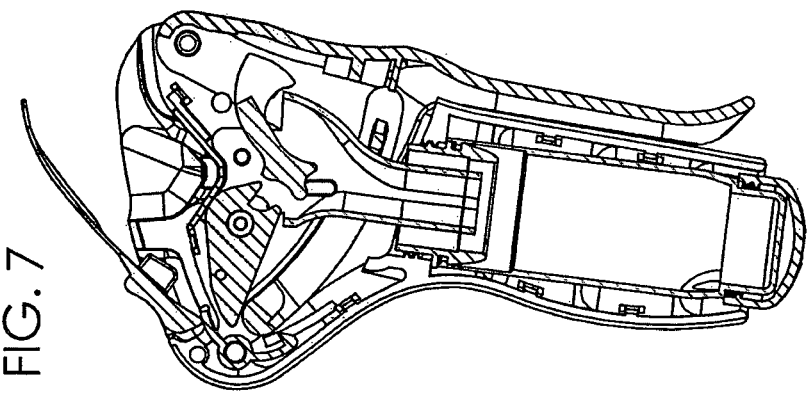

FIG. 7 is a longitudinal-section view with the upper lid in the open position.

DETAILED DESCRIPTION OF THE UTILITY MODEL

In a preferred embodiment, the compact needle remover comprises a lower portion (3) and an upper portion (4), both of them forming an anatomical body wherein said body, after having been formed, creates an internal cavity or space which is closed by a threaded safety lid (13) which also serves to fasten the container, said container (6) being inserted in said space that is why there is an upper receiving bush (5); wherein said container stores needles removed from syringes and is available after the needle remover is opened by lifting the upper lid (2), which activates the lock (7) which, in its turn, releases the lever (1), said needle remover having a lateral activating lever (1) of the upper lid (2) which allows access to the funnel-shaped mouthpiece (14) in which said needles are inserted to be removed from the plastic tip of the syringes, causing them to go through a funnel-shaped receiver (9) that forms a passageway for the container; wherein the needles are placed in said mouthpiece (14) and are guided by a metallic plate (8), containing a central orifice, until the plastic tip of said syringe reaches the bottom of the mouthpiece, thus avoiding any user effort; wherein said removal is performed by a joint movement of two parts, a beaklike part 12 and a cam 11 that form a dovetail joint, which can grip and deform the syringe needle and pull it inside the container (6); wherein said movement caused by activating the lateral lever (1) which, after removing the needle, moves a curved rode member (10) or a guide member of the beaklike part (12) that touches the rear part of the beaklike part (12) opening the dovetail joint and permitting the deformed needle drop into the container (6).

The needle remover can be carried to any place, for example, inside a pocket, thus facilitating its immediate use after administering an injection to a patient.

The container (6) can be removed from the device and disposed of as hospital waste for recycling with no major concerns. Since the remover separates the piercing portion of the plastic part, all of this material can be disposed of and recycled at a proper recycling facility.

What is claimed is:

1. Constructive arrangement applied to remover of needles from disposable syringes characterized in that the constructive arrangement comprises a lower portion (3) and an upper portion (4), both of the lower portion and the upper portion forming an anatomical body wherein said body, after having been formed, creates an internal cavity or space which is closed by a threaded safety lid (13) which also serves to fasten a container, said container (6) being inserted in said space that is why there is an upper receiving bush (5); wherein said container stores needles removed from syringes and is available after the needle remover is opened by lifting an upper lid (2), which activates a lock (7) which, in turn of the lock, releases a lever (1), said needle remover having the lever (1) of the upper lid (2) which allows access to a funnel-shaped mouthpiece (14) in which said needles are inserted to be removed from the plastic tip of the syringes, causing them to go through a funnel-shaped receiver (9) that forms a passageway for the container; wherein the needles are placed in said mouthpiece (14) and are guided by a metallic plate (8), containing a central orifice, until the plastic tip of said syringe reaches the bottom of the mouthpiece, thus avoiding any user effort; wherein said removal is performed by a joint movement of two parts, a beaklike part (12) and a cam (11) that form a dovetail joint, which can grip and deform the syringe needle and pull the syringe needle inside the container (6); wherein said movement caused by activating the lever (1) which, after removing the needle, moves a curved rode member (10) of the beaklike part (12) that touches the rear part of the beaklike part (12) opening the dovetail joint and permitting the deformed needle drop into the container (6).

\* \* \* \* \*